United States Patent
McGhee

(10) Patent No.: US 6,182,662 B1
(45) Date of Patent: Feb. 6, 2001

(54) INTRAVENOUS TRANSPORT/SUPPORT DEVICE

(76) Inventor: Chad J. McGhee, 500 E. Gore St., Orlando, FL (US) 32806

(*) Notice: Under 35 U.S.C. 154(b), the term of this patent shall be extended for 0 days.

(21) Appl. No.: 09/121,039

(22) Filed: Jul. 23, 1998

(51) Int. Cl.⁷ .................................................. A61G 15/00
(52) U.S. Cl. .......................................... 128/845; 128/877
(58) Field of Search .................................. 128/877, 878, 128/879; 24/495, 494; 403/24, 97; 248/231.4

(56) References Cited

U.S. PATENT DOCUMENTS

| | | |
|---|---|---|
| 4,738,369 | 4/1988 | Desjardins . |
| 4,854,016 * | 8/1989 | Rice ........................................ 24/495 |
| 4,886,237 | 12/1989 | Dennis . |
| 4,969,768 * | 11/1990 | Young .................................... 403/87 |
| 5,149,036 | 9/1992 | Sheehan . |
| 5,161,764 | 11/1992 | Roney . |
| 5,319,816 | 6/1994 | Ruehl . |
| 5,332,184 * | 7/1994 | Davis ................................ 248/231.4 |
| 5,499,721 | 3/1996 | Hansen et al. . |
| 5,647,491 | 7/1997 | Foster et al. . |

* cited by examiner

Primary Examiner—Michael A. Brown
(74) Attorney, Agent, or Firm—Julian C. Renfro, Esq.

(57) ABSTRACT

A support device for rapid attachment to a structural component of a bed, stretcher, gurney or the like, for supporting a device on behalf of a patient. This device comprises first and second clamping jaws operatively associated with an elongate rod, with each of the jaws having at least one active surface. A manually operable component is utilized for bringing about movement along the elongate rod of one of the jaws relative to the other jaw, with the manually operable component enabling the active surfaces of the first and second jaws to converge in a generally aligned manner. The active surfaces of the jaws are placable on either side of a structural component of a bed, stretcher, gurney or the like, with continued operation of the manually operable component causing the active jaw surfaces to bear closely against and thereafter tightly grasp the structural component and thus form a sturdy mounting for the elongate rod. The elongate rod is readily fitted with various component support devices, including devices for supporting a liquid container, a pulley system, a stirrup or an oxygen bottle.

26 Claims, 3 Drawing Sheets

INTRAVENOUS TRANSPORT/SUPPORT DEVICE

FIELD OF THE INVENTION

This invention relates to a device designed for supporting a bottle or container to be utilized for intravenous delivery of various fluids, including nutrient solutions and the like, which device obviates the use of the commonly used roller mounted IV stand, and which device also makes possible the support of various other components utilized in the healthcare field.

BACKGROUND OF THE INVENTION

Intravenous (IV) stands are in common use in hospitals, nursing homes and facilities in which patients must receive fluids while in a bed or in transport. These stands frequently are a base with wheels and a stand projecting vertically to a height above the patient, for attachment of the liquid containers to permit gravity flow of the fluid into a blood vessel of the patient. This configuration is not very stable since the stand can be rolled away form the patient unintentionally while the connecting tubes are still attached to the patient. Also the stand with the fluid container elevated above the patient is top heavy and can topple.

A further problem is the difficulty in transporting the patient and having to move the IV stand synchronously with the patient transport (e.g. bed or gurney). This is especially important in critical care units where the patient requiring intravenous infusion has been placed in a bed and must be moved while still in the same bed. Satisfactory support is also needed in a hospital room where the patient is not being transported but still requires a stable IV support arrangement permitting unimpeded access to the patient.

To overcome these problems, certain means for attaching the upright stand to the patient support have been designed. These include a rigid connector between the IV stand and the bed so that both can be rolled together. Teachings of this type include the Dennis U.S. Pat. No. 4,886,237; the Sheehan U.S. Pat. No. 5,149,036; and the Ruehl U.S. Pat. No. 5,319,816. However, these designs frequently interfere with access to the patient by the medical staff and are fixed in place, thereby limiting their utility. Also, the conventional IV stand manifestly requires a tangible amount of space alongside the patient's bed, which space would otherwise be available for other purposes.

A need clearly exists for a simple IV support device which can be readily attached to the bed or gurney upon which the patient is lying, and then easily moved to any desired position with respect to the patient. The device should also be readily affordable and capable of being stored without interfering with access to the patient.

Considering now in more detail some of the generally relevant prior art patents, it is to be seen from the Desjardins U.S. Pat. No. 4,738,369 entitled "CEILING SUPPORT FOR PATIENT MONITORING EQUIPMENT" that some efforts to avoid the use of the clumsy rollaround IV stands has involved a support arrangement for a solution bottle 22 that is suspended from the ceiling over the patient's bed. However, while making more bedside space available, such an arrangement is necessarily expensive, and would be difficult to retrofit into rooms of many hospitals of older construction.

The Dennis U.S. Pat. No. 4,886,237 entitled "UNIVERSAL ARTICULATABLE SUPPORT FOR RETAINING INTRAVENOUS STANDS IN MEDICAL APPLICATIONS" illustrates an arrangement whereby the intravenous stand 17 is stabilized by the use of a pivoted bar mounted to the frame 12 of a patient support, which obviously is a bed. This approach, however, still does not obviate the use of the archaic IV stand, which takes up space alongside the bed that could be utilized for other purposes.

The Sheehan U.S. Pat. No. 5,149,036 entitled "DEVICE FOR ATTACHING AN IV POLE TO A HOSPITAL BED OR THE LIKE" reveals another arrangement for providing stability to an IV pole 10 upon which an administration bag 17 is supported, but this is another example of the continuing use of a device requiring a tangible amount of space in the immediate vicinity of a patient's bed.

The Ruehl U.S. Pat. No. 5,319,816 entitled "IV RACK TRANSFERRABLE FROM AN IV STAND TO A HOSPITAL BED" reveals an IV rack that quite interestingly, is movable from the IV stand mounting block 24 to the IV rail mounting block 12. After the rack has been transferred to the IV rail, a handle 71 of lever 64 is raised upwardly thereby enabling the IV stand to be cleared so that it can be rolled away from the bed. This, however, is not only a manifestly expensive arrangement, but also it would not permit an IV bottle to move with the patient from one bed to another.

The Hansen et al U.S. Pat. No. 5,499,721 entitled "SUPPLY STAND CLAMP" teaches the use of multiple IV pole supporting arrangements mounted at one end of a wheeled bed, but these various mechanisms are also necessarily expensive and clearly would not permit an IV bottle to move with the patient from one bed to another.

Lastly, Foster et al U.S. Pat. No. 5,647,491 entitled "IV RACK" illustrates another arrangement in which the IV rack derives support from the ceiling. This arrangement is obviously very complicated and would necessarily involve an expense that could not be justified by a vast majority of hospitals.

It is quite obvious that none of these devices is of simple, uncomplicated construction, that can easily be attached, without the use of tools, to any selected location on a bed, stretcher or gurney; that can easily follow the patient from bed to bed; and which can provide a highly satisfactory support arrangement for any of a number of different types of drugs or fluids to be administered.

SUMMARY OF THE INVENTION

It is to be seen that the instant support device is quite suitable for rapid attachment to a structural component of a bed, stretcher, gurney, wheelchair or the like, with a primary embodiment of my novel support device enabling a bottle or bag containing an intravenous fluid such as blood products, a nutrient solution or the like to be conveniently suspended above a patient. This novel device comprises first and second clamping jaws operatively associated with an elongate rod, with each of the jaws having an active surface. The first jaw is movable with the elongate rod relative to the second jaw, and manually operable means are connected to the second jaw for causing selective movement of the first jaw relative to the second jaw. This manually operable means enables the active surface of the first jaw to approach the active surface of the second jaw, with the active surfaces of the jaws being placeable on either side of a structural component of a bed, stretcher, gurney, wheelchair or the like, with continued operation of the manually operable means causing the active jaw surfaces to bear closely against and thereafter tightly grasp the structural component. In this way a sturdy mounting is created for the elongate rod. Importantly, component support means utilized on a part of the elongate rod remote from the jaws serves in the instance of the primary embodiment as the support for a container of liquid, such as blood products, a nutrient solution or the like to be administered to a person lying on a bed, stretcher or gurney.

The elongate rod forming an intrinsic part of my novel device may be provided with a plurality of pin-receiving holes, and either end of the elongate rod may receive a sheath-like member sized to be placed in a slidable relationship with the rod. The sheath-like member fits in an encompassing manner around an end of the rod and contains therein a spaced series of pin-receiving holes of a size comparable with the pin-receiving holes of the elongate rod. In this way a selected hole of the sheath-like member may be brought into alignment with a hole in the elongate rod, with pin means being inserted in the aligned holes to achieve a sturdy mounting of the sheath-like member at a selected location on the rod.

The sheath-like member may have a variety of different component support means thereon, such as a component from which an IV solution may be suspended; a pulley arrangement adapted to be utilized in conjunction with a support of a body part of a person lying on the bed, stretcher or gurney; at least one foot-receiving stirrup adapted to be utilized in connection with a person undergoing a pelvic examination or childbirth; or for other miscellaneous functions such as supporting a clip for easy setup of a sterile drape for surgical procedures, or a small container designed to provide a disposal site for contaminated needles. A sheath-like member may be adjustably mounted on a lower portion of the elongate rod for the support of an oxygen bottle.

In each instance, the relationship of the sheath-like member to the elongate rod may be readily adjusted so that the component support means is disposed at an appropriate height with respect to the bed, stretcher, gurney or wheelchair.

With regard to the aforementioned component support means involving one or more pulleys, the typical arrangement involves a rope or other flexible member passing over the pulley or pulleys, with one end of the rope or flexible member attached to the cast or pin of a bed patient, whereas a weight is attached to the other end of the rope or flexible member. In this way the weight may serve as an effective counter balance enabling the patient to lie in a more comfortable position than would otherwise be possible, while at the same time providing traction to the extremity.

As to other component support means, whereas some beds, stretchers or gurneys are equipped with stirrup support means, some are not, so the novel configuration of my transport/support device makes it readily possible for a pair of these devices upon each of which a stirrup is mounted to be affixed in a sturdy manner to the non-equipped bed, stretcher or gurney.

Still another component support means may take the form of a support for an oxygen bottle to accompany a patient being transported on a stretcher or gurney, with the oxygen bottle typically being supported from a lower portion of the elongate rod.

It is thus to be seen that a primary object of this invention is to provide a highly effective support device of low cost, that can be readily attached to any of a number of suitable locations on a bed, stretcher, gurney or wheelchair, so as to serve in an effective manner for a component support device utilized in the support of an IV bag or bottle containing a nutrient solution, blood products, or the like, or for the mounting of devices of a mechanical nature used in the healthcare field.

Another object of this invention is to provide a readily manipulated mechanical device easily attached without the use of tools to any of a number of suitable locations on a bed, stretcher, gurney or wheelchair, thus to provide a highly effective yet affordable support device for an IV bag or bottle, or for a counterweight.

Yet another object of this invention is to provide a support device for the administration of fluids to a patient, or for the mounting of various mechanical means utilized in patient care, that is directly attachable to any of a number of suitable locations on a bed, stretcher, gurney or wheelchair, thus entirely obviating the use of the customarily used pole mounted on casters that in the past has occupied a substantial amount of space alongside a hospital bed.

Yet still another object of this invention is to provide a readily affordable support device involving an elongate rod that can be easily clamped without the use of tools to a bed, gurney, stretcher or wheelchair, to either end of which rod a sheath-like member may be quickly and adjustably attached, with such sheathlike member able to effectively serve as the mounting for various component support means of the type frequently utilized in patient care.

These and other objects, features and advantages will be apparent from a careful consideration of the appended drawings and accompanying description.

BRIEF DESCRIPTION OF DRAWINGS

FIG. 2 is a fragmentary view of a portion of the mechanism of FIG. 1, with this second figure revealing how upon manipulation of a tightening member by the attendant, certain components can be actuated so as to cause the elongate rod to move upwardly, and thus bring about the lower jaw moving in the direction of the fixed upper jaw, occasioning a highly desirable clamping action with respect to the frame of a bed or the like;

FIG. 2a is a fragmentary view of the spring biased gripping lever serving to hold the elongate rod in the position in which the jaws maintain a gripping relationship with respect to a component of a bed, wheelchair, gurney or the like;

FIG. 4 is a fragmentary view of still another construction in accordance with this invention wherein the sheath-like member atop the elongate rod serves as the support for a stirrup or footholder utilized in conjunction with a pelvic examination or childbirth; and FIG. 5 is a perspective view to a somewhat smaller scale revealing how a pair of arms can be adjustably mounted adjacent the lower part of my device, to serve as a support for an oxygen bottle or the like.

DETAILED DESCRIPTION

Figure 1:
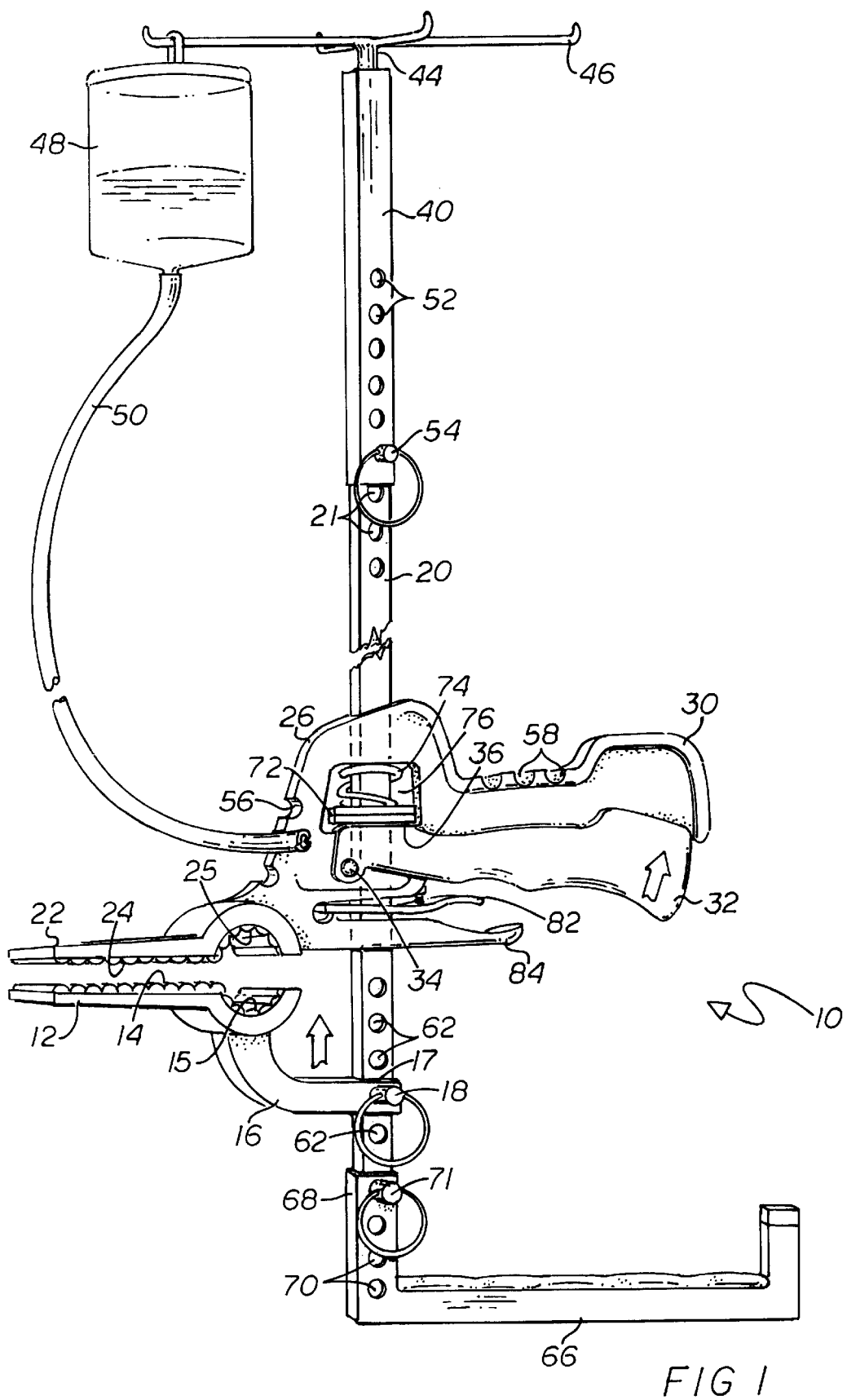
FIG. 1 is a perspective view of a primary embodiment of my invention, with this figure revealing the arrangement by which clamping jaws operatively associated with an elongate rod of adjustable height may be tightly applied to the structural member of a bed, stretcher, gurney or wheelchair, with a sheath-like member removably attached to the upper portion of the elongate rod serving in this instance as the support for an IV bottle or container.

Illustrated in FIG. 1 is a primary embodiment of a support device 10 in accordance with my invention, which is designed for rapid attachment to a structural component of a bed, stretcher, gurney or the like, or in some instances to a wheelchair. This novel device is adaptable for a variety of purposes, with one embodiment involving a sturdy and suitable support for the administration of a liquid such as an IV fluid or nutrient solution to a person lying on the bed, stretcher or gurney, and another embodiment involving a support device for a body part encased in a cast, for example. Still another embodiment can involve my device utilized for the support of a stirrup that could be rapidly attached to a bed, stretcher or gurney. The embodiment of my invention concerned with the support of a body part will be discussed hereinafter in conjunction with FIG. 3, whereas the embodiment associated with the mounting of a stirrup will be discussed hereinafter with respect to FIG. 4. The lower portion of my novel device can be utilized for the support of an oxygen bottle for example, which aspect will be discussed in conjunction with FIG. 5.

From FIG. 1 it will be seen that my novel support device 10 comprises first and second clamping jaws, jaws 12 and 22, which are configured so as to be operatively associated with an elongate rod 20 of sturdy construction. The first or lower jaw 12 has an active surface 14 and a laterally extending portion 16 attachable by member 18 to the lower end of the elongate rod 20. The end of portion 16 remote from the jaw is of a size such that it can be accommodated on the lower portion of the elongate rod 20.

More particularly, the laterally extending portion 16 is provided with an aperture 17 of a size to closely receive the lower end of the elongate rod 20. The lower end of the rod 20 is provided with a spaced series of holes or apertures 62. In addition, a single hole of approximately the same size as one of the holes 62 extends through the end of the portion 16 at the location of the aperture 17. This construction makes it possible for the attendant to readily select a desired relationship between the laterally extending member 16 and the rod 20, accomplished by the attendant aligning the single small hole in the end of member 16 with a desired one of the holes or apertures 62 located in the lower end of elongate rod 20. At this point the attendant inserts a pin 18 into the aligned holes, thus to secure the laterally extending portion 16 in a secure relationship to the rod 20.

Now with regard to the second or upper jaw 22, this jaw is equipped with an active surface 24 and a laterally extending portion 26. The portion 26 has an aperture (not visible in FIG. 1) through which the elongate rod 20 extends.

Preferably integral with the laterally extending portion 26 is a sturdy handle 30, which is adapted to be grasped by the attendant when the jaws are to be moved together, into gripping contact with a structural portion of the bed, gurney or wheelchair, as the case may be. A tightening member 32 is operatively associated with the handle 30, with the tightening member positioned so as to be contacted by the fingers of the attendant when the handle 30 is grasped. The tightening member 32, also referred to as a manually operable means, is pivotally mounted at 34 to the portion or member 26, and is configured so as to retract to some extent into an open side portion of the handle 30 at such time as the attendant tightens his or her fingers; note FIG. 2. As will be explained in detail hereinafter, by the attendant successively grasping and then releasing the tightening member or manually operable means 32, the lower or first jaw 12 can be caused to approach the upper or second jaw 22, and to tightly engage any structural component disposed between the jaws. The operation of this aspect of my device will be described at greater length hereinafter.

It will be noted in accordance with the embodiment illustrated in FIG. 1 that a sheath-like member 40 is slidably located atop the elongate rod 20, with the member 40 forming the support for a plurality of laterally extending members 46 designed to receive an IV bottle or other container, such as the bottle 48. The bottle 48 may of course contain an intravenous fluid, blood products or a nutrient solution. The members 46 have hook-shaped portions configured to receive the IV bottle or other such container. A swivel 44 mounted at the uppermost portion of the sheath-like member 40 forms the support for the laterally extending members 46, permitting any needed rotation thereof.

A spaced series of holes or apertures 52 are disposed in an aligned relationship along a lower portion of the sheath-like member 40, with these holes being provided to enable the effective height of the laterally extending members 46 to be readily adjusted. A selected one of the holes 52 can be brought into alignment with a selected one of the holes 21 placed relatively near the upper portion of the elongate rod 20. When the alignment of the desired hole 52 with a hole 21 in the rod 20 has been achieved, a pin 54 is slid into the aligned holes so as to stably support the sheath-like member 40 as well as the laterally extending members 46 in the desired height relationship.

Also revealed in FIG. 1 is a series of notches 56 provided on an upper surface of the member 26, into which the tube 50 leading downwardly from the IV bottle can be tightly inserted, thus to provide a desirable form of anchor for the tube 50. Similarly, I may utilize a spaced series of notches 58 on the upper surface of the handle 30, provided as an alternative anchoring location for the tube 50.

It will be noted that the elongate rod 20 may be of considerable length, with a lower portion thereof adapted to have the laterally extending portion 16 of the lower jaw 12 attached thereto, as was previously mentioned. Because of this arrangement it is appropriate to regard the first jaw 12 as being the movable jaw inasmuch as it necessarily moves upward to approach the second jaw 22 at such time as the tightening member or manually operable means 32 is manipulated by the attendant to cause upward movement of the elongate rod 20 relative to the handle 30.

As should now be clear, the provision of the spaced series of holes 62 along the lower portion of the elongate rod 20 permits the attendant to select the optimum mounting location for the end of the laterally extending portion 16 remote from the jaw. The holes 62 also make it possible for the height of the arm 66 to be optimized, so that it can best serve as the support for an oxygen bottle or the like. It is often necessary or desirable for a patient being moved on a stretcher or gurney to be accompanied by an oxygen bottle.

I prefer for the inboard end of the arm 66 to be provided with an upstanding or upwardly turned portion 68 in which are provided one or more holes 70. As is obvious, the attendant, after bringing one of the holes 70 in alignment with a hole 62 in the lower end of the rod 20, can insert a pin 71 so as to secure the arm 66 in a sturdy, essentially right angle relationship with the rod 20.

Figures 4, 5:
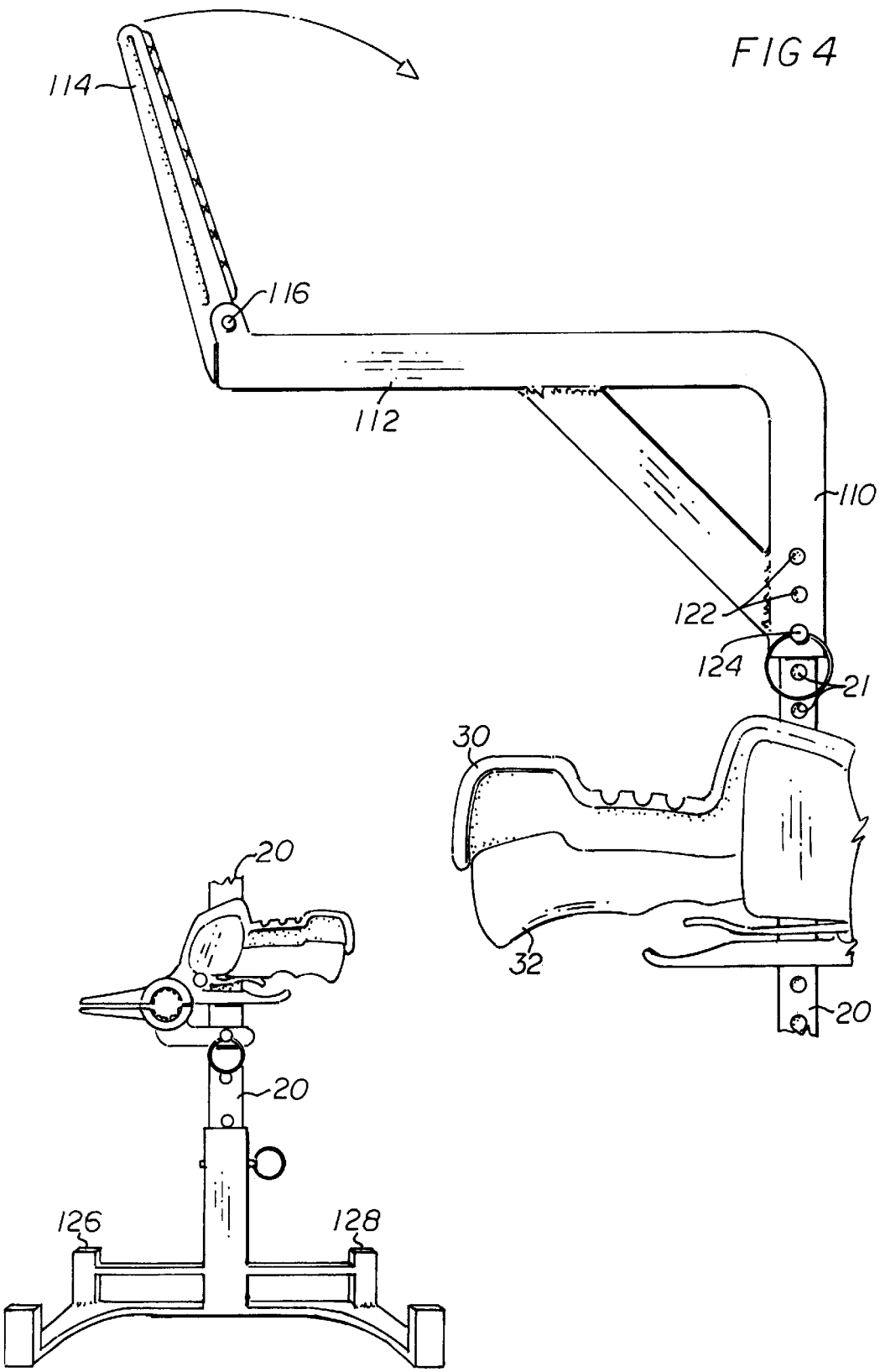

In FIG. 5 I reveal an alternative configuration of this laterally extending member, as will be discussed hereinafter.

It has already been mentioned that by an attendant grasping the handle 30 and successively pulling upward on the tightening member or manually operable means 32, the elongate rod 20 is caused to move upward, and bring about an active surface of the lower jaw 12 approaching the corresponding active surface of the upper jaw 22. In order that this can be brought about, I provide a pair of steel plates 72, visible in FIGS. 1 and 2. These plates have central apertures sized so that they will reside in a closely surrounding relationship to the elongate rod 20. The steel plates 72 are supported upon a flat upper portion 36 of the tightening member 32 in the vicinity of the pivot 34. A compression spring 74 is disposed in a suitable aperture 76 formed in the handle 30, with the several turns or coils of this spring extending around the rod 20. The upper coil of the spring 74 bears against a part of the handle 30, whereas the lower coil of the spring bears against the upper of the two steel plates 72. In this manner the spring 74 serves to bias the lower steel plate against the flat upper portion 36 of the tightening member 32. When the steel plates 72 are in the position illustrated in FIG. 1, they do not interfere with motion of the rod 20 with respect to the handle 30.

As a result of this arrangement, when the attendant grasps the fixed handle 30, his or her fingers curl around the movable tightening member 32. When the member 32 is thereafter squeezed upwardly, into the position shown in FIG. 2, the flat portion 36 of the member 32, which is relatively close to the pivot 34, tilts upwardly, thus causing the steel plates 72 to be lifted in an inclined manner against the bias of the compression spring 74. Because the plates 72 reside in a closely surrounding relationship to the elongate rod 20, the inclined raising of the plates 72 by their contact with flat portion 36 causes the tilted plates to engage the edge of elongate rod 20 sufficiently tightly that the rod 20 is forcefully raised for a distance roughly equal to the upward travel of the tightening member 32.

A gripping lever 82, located below and relatively close to the tightening member 32, is provided for holding the elongate rod 20 in each new position brought about by the efforts of the attendant in squeezing and then releasing the manually operable means 32. The construction of the gripping lever 82 will shortly be discussed in connection with FIG. 2a.

Figure 2:
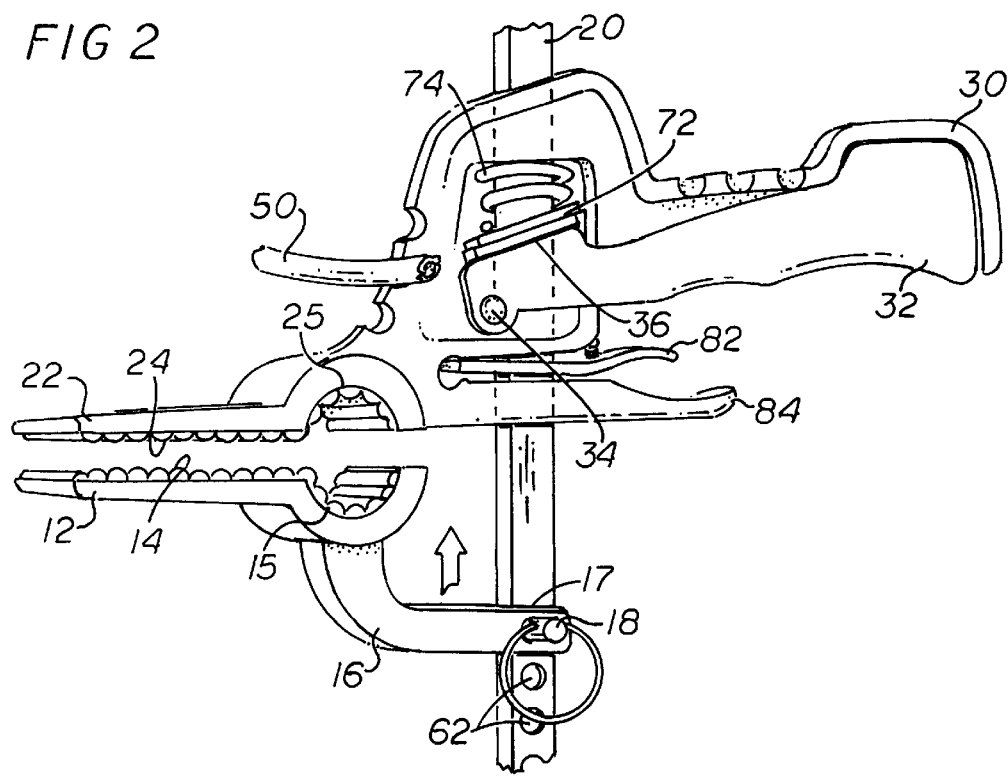

It is readily apparent that if the user holding the handle 30 pulls upon the tightening member or manually operable means 32 for a successive number of times into the position depicted in FIG. 2, the tiltable plates 72 successively engage and cause incremental upward movement of the elongate rod 20, with gripping lever 82, by virtue of its spring bias, in each instance holding the elongate rod in each new position. As will be obvious from this arrangement, this upward movement of the rod 20 relative to the handle 30 causes the active surfaces 14 and 24 of the jaws 12 and 22 to be brought more closely together. More particularly, this continued use of the tightening member 32 causes the active surface 14 of the lower jaw 12 to approach the active surface 24 of the second jaw 22 in alignment therewith. It is obvious that these active surfaces of the jaws are placeable on either side of a structural component of a bed, stretcher, gurney or the like, with continued operation of the manually operable means 32 causing the active jaw surfaces to bear closely against and thereafter tightly grasp the selected structural component and thus form a sturdy mounting for the elongate rod 20.

Figure 2A:
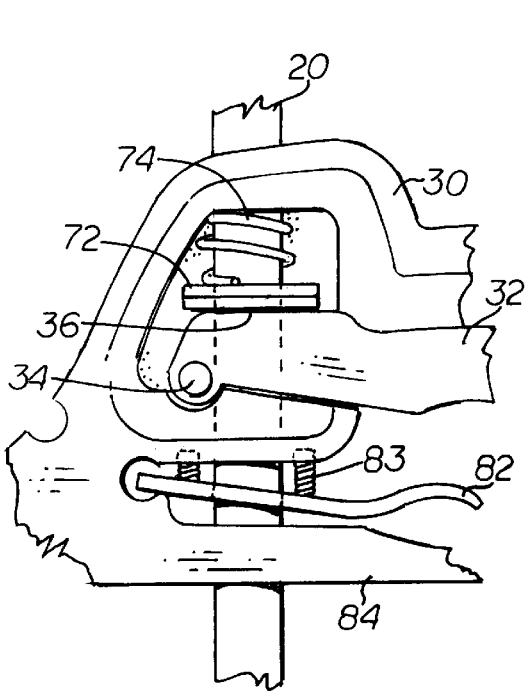

With reference to FIG. 2a it will be seen that by this fragmentary view I reveal that the inner end of the gripping lever 82 resides in a suitable small aperture in the laterally extending portion 26, with the lever 82 being movable for a limited extent from the position in which it is depicted. The lever 82 has a central aperture sized so that it will reside in a closely surrounding relationship with respect to the elongate rod 20, and is normally biased downwardly by one or more small compression springs 83 such that the lever 82 normally resides in an angled relationship with the rod 20.

The angled relationship of the lever 82 is such as to cause an interior edge of the lever 82 to engage the edge of elongate rod 20 sufficiently tightly that the rod 20 will not slip downwardly. However, the gripping lever does not interfere with the elongate rod 20 moving upwardly with each new squeeze of the manually operable means 32, with the gripping lever 82 automatically holding the rod 20 in each new position of tightness.

It is obvious that provision must be made for the release of the jaws from a clamping relationship with respect to a structural component, and this can be accomplished by the attendant pulling upward on the gripping lever 82, so as to overcome the bias of the small springs 83. Upon the attendant causing the lifting of the lever 82, the interior edge of the lever 82 is removed from gripping contact with the edge of the elongate rod, thus releasing the rod and permitting it to move downwardly under the influence of gravity.

It was previously explained that the compression spring 74 presses downwardly upon the steel plates 72, and when the manually operable means is not being grasped, the flat upper portion 36 of the tightening member 32 is in the perpendicular relationship to the elongate rod 20 depicted in FIG. 1. This action of the spring 74 causes the steel plates to also reside in a perpendicular relationship to the elongate rod 20, in which position they do not interfere with movement of the elongate rod 20 in the release direction.

As previously mentioned, laterally extending members 46, serving as component support means, are mounted on a sheath-like member 40 on a portion of the elongate rod 20 remote from the jaws, with the laterally extending members 46 as well as a bottle supported therefrom necessarily moving upwardly contemporaneously with the upward movement of the lower jaw 12.

It is apparent that care must be taken to prevent the rapid descent of the laterally extending members 46, so the attendant is cautioned to have one hand on the elongate rod 20 to steady same at such time as the gripping lever 82 is pulled to bring about release of the elongate rod from its raised position.

To prevent an undesirable sudden release of the steel plates 72 from the rod-gripping relationship, I provide a guard member 84 relatively close to the gripping lever 82, with the guard member being rigid and preferably integral with the upper jaw 22 and the laterally extending portion 26. These components may for example be made of industrial grade plastic, although I am not to be limited to this.

Also, I am not to be limited to the use of substantially flat active surfaces 14 and 24 of the jaws, for as illustrated in FIGS. 1 and 2, I may also utilize a circular portion 15 in the first jaw 12, and a circular portion 25 in the second jaw 22, with these circular surfaces being internally toothed and disposed in substantial alignment with each other. These circular surfaces may be covered with rubber or plastic, and the provision of these surfaces makes it possible for my novel device to be readily clamped to a round structural member, such as the arm of a wheelchair or the like.

Figure 3:
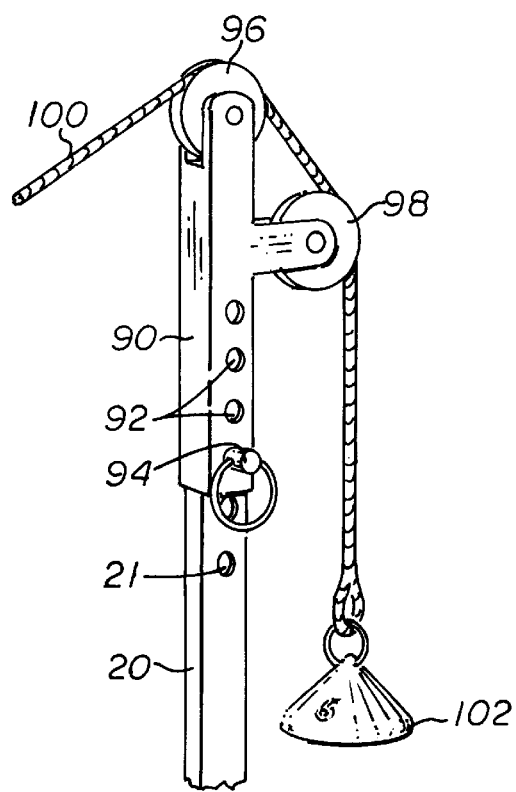
FIG. 3 is a fragmentary view of an alternative construction wherein the sheath-like member accommodated atop the elongate rod serves as the mounting means for a pair of pulleys over which the rope or other flexible member associated with a counterweight can pass.

Although an important use of my device is for the support of an IV bottle or the like, I am manifestly not to be limited to this, and with reference to FIG. 3 it will be noted that I may utilize a sheath-like member 90 that is adapted to be placed in a surrounding relationship atop the elongate rod 20. An aligned series of holes 92 resides along a portion of the length of this sheath-like member, whereas one or more holes 21 may be utilized in the upper end of the rod 20. In a manner generally similar to the explanation provided in connection with the embodiment depicted in FIG. 1, when the sheath-like member 90 has been brought to a desired height, a pin 94 can be inserted into a selected one of the holes 92 when that selected hole is in aligned relationship with the hole in the upper portion of the rod 20, thus securing the sheath-like member 90 in a desired height relationship to the bed in which the patient may be residing.

FIG. 3 reveals that the sheath-like member 90 forms the support for an upper pulley 96 and a side pulley 98, with a rope 100 arranged to pass over these rotatably mounted pulleys. As is obvious, I am not to be limited to a rope, for a cable or other flexible member may be used as the member 100.

One end of the rope or cable 100 may be attached to a weight 102, whereas the other end of the rope or cable may be attached to the cast of a patient, so that the weight 102 can serve as a counterbalance for the weight of the cast, thus permitting the patient to lie in a relatively comfortable position while at the same time traction is applied to the injured extremity. Another possibility is that the end of the rope remote from the weight 102 may be attached to a pin that has been inserted into a large bone of the patient, thus to serve the purpose of minimizing the weight of the affected part.

Turning now to FIG. 4, another embodiment of my novel support device is illustrated, involving a sheath-like member 110 that, like the other sheath-like members, is adapted to be mounted atop the elongate rod 20. The upper portion of the sheath-like member 110 has a 90° bend so as to provide a laterally extending portion 112. The laterally extending portion 112 may for example be 12" in length, although I obviously am not to be limited to this.

Attached to the laterally extending portion 112 at a location remote from the member 110 is a footholder or stirrup 114, which is preferably attached by a pivot 116 to the laterally extending portion 112. This arrangement permits the stirrup portion 114 to be folded over atop the portion 112 when not in use.

Whereas some beds, stretchers and gurneys are provided with stirrups, others are not, so this embodiment of my invention reveals a highly advantageous arrangement whereby a pair of my novel support devices can be used to readily provide a pair of stirrups to a non-equipped bed, stretcher or gurney.

As is obvious, a pair of stirrups 114 may be provided for use by a patient undergoing a pelvic examination or childbirth, with the use of the stirrups requiring each of the sheath-like members 110 associated with a stirrup to be disposed relatively close to the respective upper clamp. To make this possible, it is necessary for the attendant to remove the pin 18 illustrated in FIG. 1, thus to enable the upper end of each elongate rod 20 to be brought relatively close to the respective portion 26 and the handle 30. Otherwise, the part of rod 20 extending above the bed would be too long insofar as the proper support of stirrups is concerned. After the upper part of the rod 20 has been brought to appropriate height above the bed, the attendant then brings the hole in laterally extending portion 16 into alignment with a new hole in the rod 20 and then reinserts the pin 18. In this way the lower jaw 12 is secured in the appropriate relationship with the laterally extending stirrup portion 112.

At this point the attendant brings one of the holes 122 in the sheath-like member 110 into alignment with one of the holes 21 in the rod 20 and then inserts the pin 124 therein, so as to secure the stirrup or footholder 114 at a desirable height with respect to the bed, stretcher or gurney.

With reference to FIG. 5, I have shown an embodiment of my invention wherein the lower portion of the rod 20 receives a sheath-like member upon which is mounted a laterally extending left arm 126 and a laterally extending right arm 128. These arms are spaced far enough apart as to permit an oxygen canister or the like to be stably supported thereon. To prevent metal-to-metal contact, I typically sheath the inner surfaces of the arms 126 and 128 with plastic or rubber. The provision of the arms 126 and 128 makes it readily possible for the oxygen canister of a patient needing oxygen to be transported directly with the gurney or stretcher upon which the patient is being carried.

As should now be obvious, I have provided a highly advantageous support arrangement suitable for use at the bedside of a patient in need of receiving IV fluid or nutrient solution, or in need of his or her cast being counterbalanced by a suitable weight. My novel support arrangement makes it unnecessary to utilize a roller mounted IV support pole adjacent a patient's bed, thus freeing up such space for other purposes.

It should be further obvious that my novel device is also usable, without substantial modification, for other purposes such as a pair of my devices being utilized for supporting foot stirrups needed by a person undergoing pelvic examination or childbirth, or for additional purposes such as supporting clips to be utilized for fast, easy setup of a sterile drape for surgical procedures. A still further utilization can be for the support of a small box serving as a disposal site for contaminated needles.

It should now be clear that my novel support device is easy to apply to a structural member of a bed, wheelchair or the like, with no tools being involved and with height adjustments readily accomplished. Immediate removal of the support device from the bed or wheelchair after it has served its need is easily accomplished.

I claim:

1. A support device for rapid attachment to a structural component of a bed, stretcher or gurney, for supporting a device on behalf of a patient, said device comprising first and second clamping jaws operatively associated with an elongate rod, each of said jaws having at least one active surface, said first jaw being movable along said elongate rod relative to said second jaw, manually operable means for causing selective movement of said first jaw along said elongate rod relative to said second jaw, with said manually operable means enabling said active surface of said first jaw to approach the active surface of said second jaw in general alignment therewith, said active surfaces of said jaws including both flat members as well as circular members, with said jaws being placable on either side of a structural component of a bed, stretcher or gurney, with continued operation of said manually operable means causing said active jaw surfaces to bear closely against and thereafter tightly grasp the structural component and thus form a sturdy mounting for said elongate rod, and component support means on a part of said elongate rod remote from said jaws.

2. The support device for rapid attachment to a structural component of a bed, stretcher, or gurney as recited in claim 1 wherein said component support means forms the support for a container of liquid to be administered to a person lying on a bed, stretcher or gurney.

3. The support device for rapid attachment to a structural component of a bed, stretcher, or gurney as recited in claim 2 in which the height relationship of said component support means with respect to said jaws can be readily adjusted.

4. The support device for rapid attachment to a structural component of a bed, stretcher, or gurney as recited in claim 1 wherein said component support means forms the support for a pulley arrangement adapted to be utilized in conjunction with the support of a body part of a person lying on a bed, stretcher or gurney.

5. The support device for rapid attachment to a structural component of a bed, stretcher, or gurney as recited in claim 4 in which the height relationship of said component support means with respect to said jaws can be readily adjusted.

6. The support device for rapid attachment to a structural, component of a bed, stretcher, or gurney as recited in claim 1 wherein said component support means forms the support for at least one foot-receiving stirrup adapted to be utilized in connection with a person undergoing a pelvic examination or childbirth.

7. The support device for rapid attachment to a structural component of a bed, stretcher, or gurney as recited in claim 6 in which the height relationship of said component support means with respect to said jaws can be readily adjusted.

8. A support device for rapid attachment to a structural component of a bed, stretcher, or gurney or wheelchair, for supporting a device on behalf of a patient, said device comprising first and second clamping jaws operatively associated with an elongate rod, each of said jaws having at least one active surface, said elongate rod having a plurality of attachment locations thereon, said attachment locations involving a series of pin-receiving holes for enabling said first jaw to be supported at a location on said elongate rod selected by a user, with said first jaw being movable with said elongate rod relative to said second jaw such that said active jaw surfaces can be brought into general alignment, manually operable means operatively associated with said second jaw for enabling the user to cause selective movement of said first jaw with said elongate rod relative to said second jaw, with said manually operable means enabling an active surface of said first jaw to approach the corresponding active surface of said second jaw, said active surfaces of said jaws being placable on either side of a structural component of a bed, stretcher, or gurney or wheelchair, with continued operation of said manually operable means causing said active jaw surfaces to bear closely against and thereafter tightly grasp the structural component and thus form a sturdy mounting for said elongate rod, said elongate rod being intended for installation in a generally vertical attitude, and component support means disposed on an upper part of said elongate rod, at a location remote from said jaws.

9. The support device for rapid attachment to a structural component of a bed, stretcher, gurney or wheelchair as recited in claim 8 in which said component support means serves as the support for a container of liquid to be administered to a patient.

10. The support device for rapid attachment to a structural component of a bed, stretcher, gurney or wheelchair as recited in claim 9 in which the height relationship of said component support means with respect to said jaws can be readily adjusted.

11. The support device for rapid attachment to a structural component of a bed, stretcher, gurney or wheelchair as recited in claim 8 in which said component support means serves as the support for a pulley arrangement adapted to be utilized in conjunction with the support of a body part of a patient.

12. The support device for rapid attachment to a structural component of a bed, stretcher, gurney or wheelchair as recited in claim 11 in which the height relationship of said component support means with respect to said jaws can be readily adjusted.

13. The support device for rapid attachment to a structural component of a bed, stretcher, gurney or wheelchair as recited in claim 8 in which said active surfaces of said jaws include both flat members as well as circular members, such that flat structural components as well as round circular components of a bed, stretcher, or gurney or wheelchair can be grasped by a corresponding pair of said active surfaces.

14. A support device for rapid attachment to a structural component of a bed, stretcher or gurney for supporting a device on behalf of a patient, said device comprising first and second clamping jaws operatively associated with an elongate rod, each of said jaws having at least one active surface, manually operable means for causing selective movement of said first jaw along said elongate rod relative to said second jaw, and in general alignment with said second jaw, said active surfaces of said jaws being placable on either side of a structural component of a bed, stretcher or gurney, with continued operation of said manually operable means causing said active jaw surfaces to bear closely against and thereafter tightly grasp the structural component and thus form a sturdy mounting for said elongate rod, said elongate rod having thereon a plurality of pin-receiving holes, and at least one sheath member sized to be inserted upon said elongate rod, said sheath member having therein a spaced series of pin-receiving holes of a size comparable with said pin-receiving holes in said elongate rod, said sheath member having component support means thereon and being slidably adjustable with respect to said elongate rod, such that a selected hole of said sheath member can be brought into alignment with a hole in said elongate rod, and pin means enabling said sheath member to be secured at a selected location with respect to said elongate rod.

15. The support device for rapid attachment to a structural component of a bed, stretcher, or gurney as recited in claim 14 wherein said component support means serves as the support for a container of liquid or food to be administered to a person lying on a bed, stretcher or gurney.

16. The support device for rapid attachment to a structural component of a bed, stretcher, or gurney as recited in claim 14 wherein said component support means serves as the support for a pulley arrangement adapted to be utilized in conjunction with the support of a body part of a person lying on a bed, stretcher or gurney.

17. The support device for rapid attachment to a structural component of a bed, stretcher, or gurney as recited in claim 14 wherein said component support means serves as the support for at least one foot-receiving stirrup adapted to be utilized in connection with a person undergoing a pelvic examination or childbirth.

18. The support device for rapid attachment to a structural component of a bed, stretcher, or gurney as recited in claim 14 wherein said component support means is attached to a lower portion of said elongate rod and serves as the support for an oxygen bottle.

19. The support device for rapid attachment to a structural component of a bed, stretcher, or gurney as recited in claim 14 in which said active surfaces of said jaws include both flat members as well as circular members, such that flat structural components as well as round circular components of a bed, stretcher, or gurney can be grasped by a corresponding pair of active surfaces.

20. A support device for rapid attachment to a structural component of a bed, stretcher, gurney or wheelchair, for supporting a device on behalf of a patient, said device comprising first and second clamping jaws operatively associated with an elongate rod, said elonaate rod having a series of pin-receiving holes therein, thus enabling the user to select the location on said elongate rod upon which said first jaw can be mounted, each of said jaws having at least one active surface, said first jaw being movable with said elongate rod relative to said second jaw such that said active surfaces can be brought into general alignment, manually operable means operatively associated with said second jaw for causing selective movement of said first jaw and said elongate rod relative to said second jaw, with said manually operable means enabling an active surface of said first jaw to approach the corresponding active surface of said second jaw, said active surfaces of said jaws being placable on either side of a structural component of a bed, stretcher, or gurney or wheelchair, with continued operation of said manually operable means causing said active jaw surfaces to bear closely against and thereafter tightly grasp the structural component and thus form a sturdy mounting for said elongate rod, said elongate rod being intended for installation in a generally vertical attitude, and a pair of component support means, with one of said component support means operatively disposed on an upper portion of said elongate rod, and the other of said component support means operatively disposed on a lower portion of said elongate rod, with said jaws being disposed at a location intermediate said component support means.

21. The support device for rapid attachment to a structural component of a bed, stretcher, or gurney or wheelchair as recited in claim 20 in which the height relationship of said one component support means with respect to said jaws can be readily adjusted.

22. The support device for rapid attachment to a structural component of a bed, stretcher, gurney or wheelchair as recited in claim 21 in which said one component support means may serve as the support for a container of liquid, such liquid to be administered to a patient through a flexible tube operatively associated with the container.

23. The support device for rapid attachment to a structural component of a bed, stretcher, gurney or wheelchair as recited in claim 22 in which said second jaw is attached to a component of said manually operable means, and a plurality of notches are provided on said component, said notches serving as means for releasably securing the flexible tube operatively associated with the container of liquid, thus to anchor the tube.

24. The support device for rapid attachment to a structural component of a bed, stretcher, gurney or wheelchair as recited in claim 20 in which the height relationship of said other component support means with respect to said jaws can be readily adjusted.

25. The support device for rapid attachment to a structural component of a bed, stretcher, gurney or the like as recited in claim 24 wherein said other component support means may serve as the support for an oxygen bottle.

26. The support device for rapid attachment to a structural component of a bed, stretcher, gurney or wheelchair as recited in claim 20 in which said active surfaces of said jaws include both flat members as well as circular members, such that flat structural components as well as round circular components of a bed, stretcher, gurney or the like can be grasped by a corresponding pair of active surfaces.

* * * * *